US00PP10316P

United States Patent [19]

Dorman

[11] Patent Number: Plant 10,316

[45] Date of Patent: Apr. 7, 1998

[54] SALVIA PLANT NAMED 'ROSE FOUNTAINS'

[75] Inventor: Carrie Lou Dorman, Temple Terrace, Fla.

[73] Assignee: Charlie's Plant Farm, Thonotosassa, Fla.

[21] Appl. No.: 672,714

[22] Filed: Jun. 28, 1996

[51] Int. Cl.[6] ..... A01H 5/00

[52] U.S. Cl. ..... Plt./54.1

[58] Field of Search ..... Plt./54.1, 68.1

*Primary Examiner*—James R. Feyrer
*Attorney, Agent, or Firm*—C. A. Whealy

[57] ABSTRACT

A distinct cultivar of Salvia plant named 'Rose Fountains', characterized by its weeping, spreading, sprawling growth habit; vigorous and rapid growth rate; and bright rose red flower color.

2 Drawing Sheets

The present invention relates to a new and distinct cultivar of Salvia plant, botanically known as *Salvia splendens* and referred to by the cultivar name 'Rose Fountains'.

The new cultivar is a spontaneous mutation of the commercial cultivar 'Purple Fountains' (not patented). The new cultivar was discovered and selected by the inventor in Tampa, Fla., in a controlled environment as a single plant among a population of plants of the cultivar 'Purple Fountains.' This single plant consistently formed inflorescences having bright rose red-colored flowers in contrast to the dark purple-colored flowers of plants of the cultivar 'Purple Fountains'.

Asexual reproduction of the new cultivar by terminal cuttings taken at Thonotosassa, Fla., has shown that the unique features of this new Salvia are stable and reproduced true to type in successive generations.

The following traits have been repeatedly observed and are determined to be the unique characteristics of 'Rose Fountains'. These characteristics in combination distinguish 'Rose Fountains' as a new and distinct cultivar:

1. Weeping, spreading, sprawling growth habit. Plants can be grown as hanging basket or patio container plants.
2. Vigorous and rapid growth rate.
3. Bright rose red flower color.

The cultivar Rose Fountains has not been observed under all possible environmental conditions. The phenotype may vary somewhat with variations in environment such as temperature and light intensity, without, however, any variance in genotype.

The accompanying colored photographs illustrate the overall appearance of the new cultivar, showing the colors as true as it is reasonably possible to obtain in colored reproduction of this type.

The first photograph comprises a top perspective view of a typical flowering plant of 'Rose Fountains'.

The second photograph comprises a close-up view of leaves and flowers of the cultivar 'Rose Fountains.'

In the following description, color references are made to The Royal Horticultural Society Colour Chart except where general terms of ordinary dictionary significance are used. The following observations and measurements describe plants grown in Thonotasassa, Fla., in a polyethylene-covered greenhouses with day temperatures ranging from 21 to 32C and night temperatures ranging from 16 to 27C.

Botanical classification: *Salvia splendens* cultivar 'Rose Fountains.'

Commercial use: Perennial shrub, appropriate for hanging basket or 15-cm patio containers.

Parentage: Spontaneous mutation of the cultivar 'Purple Fountains' (not patented).

Propagation:

*Type.*—Terminal tip cuttings.

*Time to rooting.*—Summer: 10 days with soil temperatures of 27C. Winter: 14 days with soil temperatures of 16C.

*Rooting habit.*—Fine, fibrous and freely branching.

Plant description:

*Form.*—Weeping, spreading and sprawling, can be grown as a hanging basket or patio container plant.

*Growth rate.*—Vigorous, rapid growth rate. Under optimal environmental conditions, from a rooted cutting, a 20-cm hanging basket can be produced in about ten weeks.

*Branching.*—Lateral branches are present at each leaf axil. Removal of terminal apices enhances the development of lateral branches.

*Plant height.*—From soil level, 30 to 45 cm.

*Lateral branch length.*—45 to 60 cm.

*Internode length.*—3.75 to 5 cm.

*Foliage description.*—Leaves arranged oppositely, single, generally symmetrical, abundant, and flat in aspect. Leaf size: Length: About 5 cm. Width: About 3 cm. Shape: Ovate. Tip: Acute. Base: Obtuse. Texture: Glossy, smooth glabrous. Margin: Serrated. Venation pattern: Pinnate. Veins prominent on under surface. Color: Young foliage, upper side: 137B. Young foliage, under side: 144A. Mature foliage, upper side: 137A. Mature foliage, under side: 147B. Petiole: Length: 1.25 to 2 cm. Color: 144A.

Flower description:

*Flower type and habit.*—Tubular bilabiate flowers borne singly on terminal racemes. Freely flowering. Flowers persistent.

*Natural flowering season.*—Flower continuously spring through fall.

*Quantity of flowers.*—24 to 30 per raceme.

*Flower length.*—2 to 2.5 cm.

*Flower width.*—5 to 7 mm.

*Flower longevity on plant.*—10 to 15 days.

*Flower longevity as cut flower.*—2 to 3 days.

*Flower buds.*—Size: Length: 1.25 to 2 mm. Width: 5 to 7 mm. Color: Slightly more red than 57A.

*Petals.*—Size: Length: 2 to 2.5 cm. Width: 5 to 7 mm. Texture: Smooth, velvety. Margin: Entire. Color: When opening: Slightly more red than 57A. Mature: Lips: 57A. Throat: 57D. Tube: 57C. Base: 155D.

*Calyx.*—Fused funnel. Size: Length: About 4 mm. Width: About 2 mm. Texture: Glabrous. Color: 144A.

*Peduncles.*—Aspect: Strong, but flexible, drooping. Length: About 2 mm. Texture: Glabrous. Color: 144A.

*Reproductive organs.*—Androecium: Stamens: Number: Four. Length: 2.5 mm. longer than floral tube. Anthers: Size: About 1 mm. Color: White. Pollen: Moderate, white in color. Gynoecium: Pistil number: One. Style color: White. Stigma shape: Bulbous.

Disease resistance: No known Salvia diseases observed to date on plants grown under commercial greenhouse conditions.

Seed production: Seed production has not been observed.

It is claimed:

1. A new and distinct cultivar of Salvia plant named 'Rose Fountains', as illustrated and described.

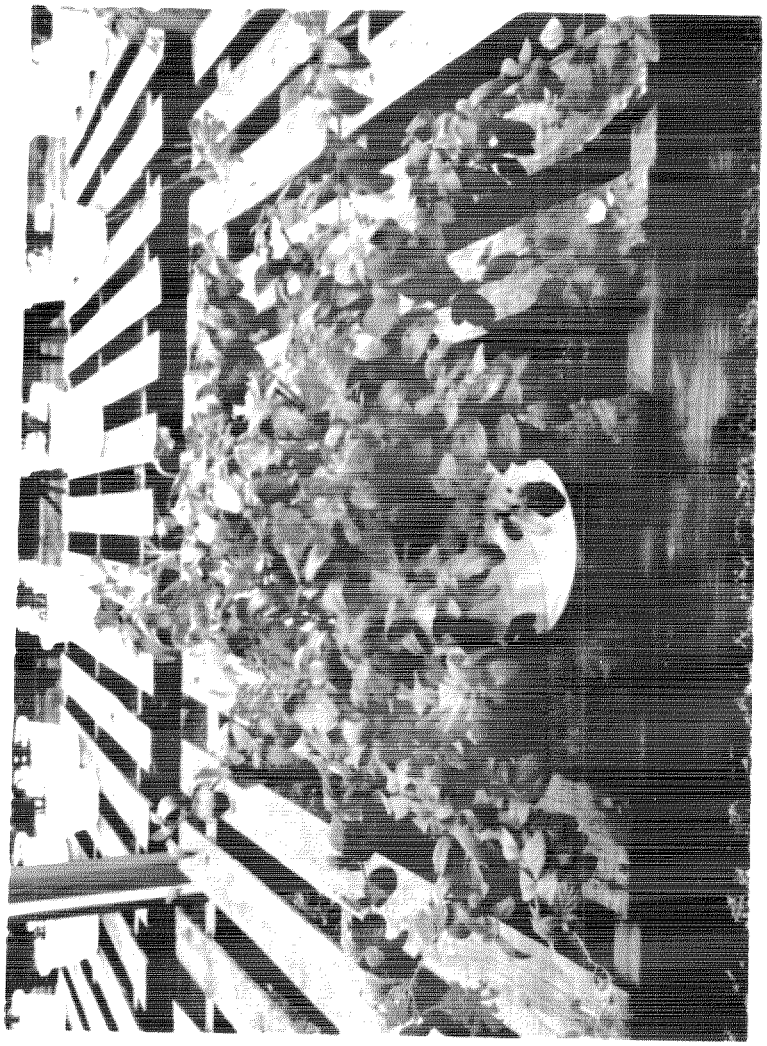

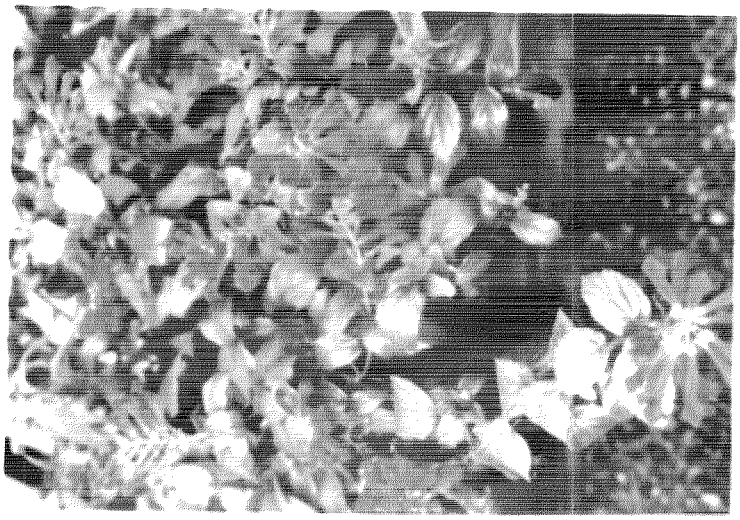

* * * * *